(12) United States Patent
Eggert

(10) Patent No.: US 10,040,808 B2
(45) Date of Patent: Aug. 7, 2018

(54) SILANE-MODIFIED FORMAMIDES

(71) Applicant: Covestro Deutschland AG, Leverkusen (DE)

(72) Inventor: Christoph Eggert, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/112,326

(22) PCT Filed: Jan. 26, 2015

(86) PCT No.: PCT/EP2015/051439
§ 371 (c)(1),
(2) Date: Jul. 18, 2016

(87) PCT Pub. No.: WO2015/113919
PCT Pub. Date: Aug. 6, 2015

(65) Prior Publication Data
US 2016/0340372 A1 Nov. 24, 2016

(30) Foreign Application Priority Data
Jan. 31, 2014 (EP) ..................................... 14153501

(51) Int. Cl.
| | |
|---|---|
| *C07F 7/02* | (2006.01) |
| *C07F 7/18* | (2006.01) |
| *C08G 18/73* | (2006.01) |
| *C08G 18/76* | (2006.01) |
| *C08G 18/78* | (2006.01) |
| *C08G 18/80* | (2006.01) |
| *C08G 18/12* | (2006.01) |
| *C09D 175/04* | (2006.01) |
| *C08G 18/28* | (2006.01) |
| *C08G 18/48* | (2006.01) |
| *C08G 18/10* | (2006.01) |
| *C09D 183/16* | (2006.01) |
| *C09J 183/16* | (2006.01) |

(52) U.S. Cl.
CPC ............ *C07F 7/1804* (2013.01); *C07F 7/184* (2013.01); *C07F 7/1836* (2013.01); *C07F 7/1888* (2013.01); *C08G 18/10* (2013.01); *C08G 18/12* (2013.01); *C08G 18/289* (2013.01); *C08G 18/4804* (2013.01); *C08G 18/73* (2013.01); *C08G 18/7621* (2013.01); *C08G 18/7831* (2013.01); *C08G 18/8019* (2013.01); *C09D 175/04* (2013.01); *C09D 183/16* (2013.01); *C09J 183/16* (2013.01)

(58) Field of Classification Search
CPC ......... C07F 7/18; C08G 18/10; C09D 183/16; C09J 175/04; C09J 183/16
USPC ........................................................ 556/414
See application file for complete search history.

(56) References Cited

U.S. PATENT DOCUMENTS

| | | |
|---|---|---|
| 4,499,150 A | 2/1985 | Dowbenko et al. |
| 4,697,009 A | 9/1987 | Deschler et al. |
| 6,730,768 B2 | 5/2004 | Heidbreder et al. |

FOREIGN PATENT DOCUMENTS

| | | |
|---|---|---|
| DE | 3524215 A1 | 1/1987 |
| EP | 0689556 A1 | 1/1996 |
| EP | 0937110 A1 | 8/1999 |
| WO | WO-9421702 A1 | 9/1994 |
| WO | WO-9821255 A1 | 5/1998 |

OTHER PUBLICATIONS

Ran et al., J. Sep. Sci. 2012, 35, 1854-1862.*
International Search Report for PCT/EP2015/051439 dated Mar. 31, 2015.

* cited by examiner

Primary Examiner — Sudhakar Katakam
Assistant Examiner — Kofi Adzamli
(74) Attorney, Agent, or Firm — Drinker Biddle & Reath LLP

(57) ABSTRACT

The invention relates to novel silane-modified formamide-polymers and/or pre-polymers for bonding and/or sealing diverse substrate materials, such as, for example metal, wood, glass and/or plastic. The invention also relates to a reactive single-component adhesive system comprising the claimed silane-modified formamide polymers.

15 Claims, No Drawings

SILANE-MODIFIED FORMAMIDES

CROSS-REFERENCE TO RELATED APPLICATIONS

This application is a national stage application (under 35 U.S.C. § 371) of PCT/EP2015/051439, filed Jan. 26, 2015, which claims benefit of European Application No. 14153501.3, filed Jan. 31, 2014, both of which are incorporated herein by reference in their entirety.

TECHNICAL FIELD OF THE INVENTION

The present invention relates to novel silane-modified formamide prepolymers of formula (I) and of formula (IV) for the coating, adhesive bonding and/or sealing of various substrate materials, such as, for example, metal, wood, glass and/or plastics material. There is additionally provided a reactive one-component adhesive system comprising the silane-modified formamide prepolymers of formula (I) and/or of formula (IV) according to the invention.

BACKGROUND OF THE INVENTION

Silane-modified polymers have generally been known for many years, and sealing materials or adhesives based on silane-modified prepolymers or polymers have proved to be successful for a very wide variety of applications, for example in seam sealing in automotive construction, in windows or in the structural facings sector.

Very generally, silane-modified polymers (which are in the form of prepolymers prior to processing) are understood as being polymers which comprise silane groups having hydrolysable radicals and the polymer backbone of which is not composed substantially of O—Si—O—Si chains, as is the case with silicones, but of C—C chains, which in most cases are interrupted by heteroatoms and further comprise urethane, ether, ester, urea, amide and other structural units. Under the action of moisture, the radicals on the silane groups, for example usually acetate or alkoxy groups, are hydrolysed with the formation of reactive silanols, which subsequently condense and cure, with water, alcohol or acetic acid cleavage, to form a high molecular weight network.

The value of these silane-modified polymers is substantially their particular property profile. On the one hand, coating materials, adhesives or sealing materials that comprise silane-modified polymers are distinguished by strong adhesion to a very wide variety of substrates without complex pretreatment (no primer is necessary). This is because OH groups are normally present on inorganic substrate surfaces and are able to react with the reactive silanols of the polymer, which form under the action of moisture. On the other hand, the properties of the silane-modified polymers can be adapted to a large number of very different applications with the aid of the polymer backbone.

The silane-modified polyurethanes and polyureas that are currently available commercially on the market are thus based on a high molecular weight backbone which is produced (i) by reaction of NCO-containing prepolymers with aminosilanes or (ii) by reaction of OH-terminated prepolymers, such as, for example, polyethers, polyurethanes or polyesters, with NCO-functional silanes, as is shown in the following formula scheme:

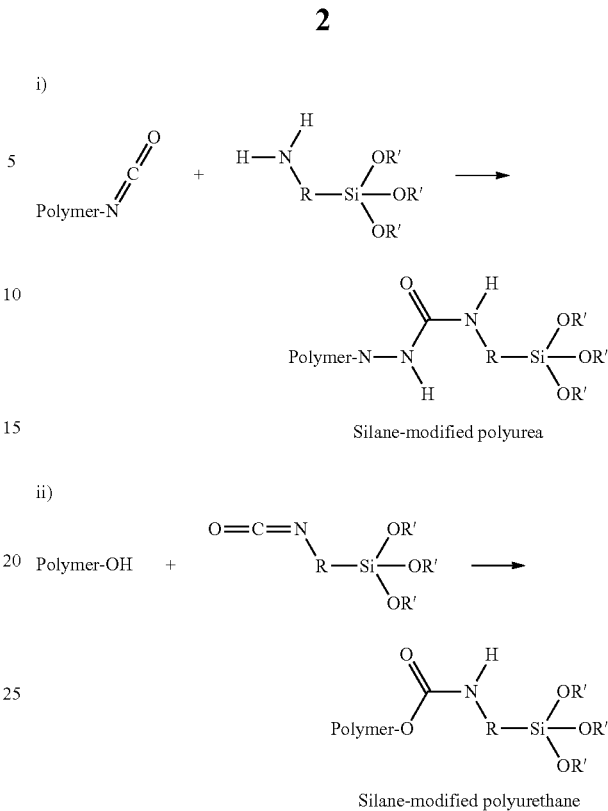

Silane-modified polyurea

Silane-modified polyurethane

A disadvantage of coating materials, adhesives and sealing materials that are based on silane-modified polyureas is, however, the high viscosity of their prepolymers. On account of the high viscosity, the use of silane-modified polyureas is possible to only a limited extent, because the coating or sealing materials to be used must normally be applied in the liquid to pasty state to the substrate parts that are to be coated or adhesively bonded. A prepolymer that is too viscous is consequently difficult or impossible to use as a coating material, adhesive and/or sealing material.

Furthermore, the degree of hardness of the resulting coating, adhesive bond and/or seal as the end product after the silane crosslinking is critical for the particular use in question. In the case of silane-modified polyureas, end products having a high degree of hardness are normally obtained. Silane-modified polyurethanes, on the other hand, provide, softer end products after curing. However, the synthesis of silane-modified polyurethanes having a high silane content is difficult to carry out economically because of the relatively expensive NCO-functionalised silane precursors.

The monomeric NCO content in silane-modified polymers additionally plays an important role in this connection: on account of the not negligible vapour pressure of the isocyanates (even at room temperature), isocyanate vapours that can be harmful to health or at least sensitising can form even during spray application. Consequently, the development of reactive prepolymers which are substantially free of isocyanate monomers and in any case are below the exposure limit value (Total Reactive Isocyanate Group concentration TRIG) according to the Technical Rules for Hazardous Substances (TRGS) 430 (edition March 2009) of 0.018 mg/m$^3$ NCO, preferably below 0.01 mg/m$^3$, particularly preferably below 0.001 mg/m$^3$, is desirable.

OBJECT OF THE PRESENT INVENTION

The object underlying the present invention is accordingly to provide an improved reactive one-component adhesive and/or coating system of inexpensive and readily accessible starting materials, which system is as harmless to health as possible and largely avoids the above-described problems of known silane-modified polymers.

There is provided in particular a reactive one-component adhesive system which is simpler to handle on account of a lower viscosity and lower crystallinity and which at the same time permits high chemical stability of the end products. Also desired are polymeric end products which can be prepared inexpensively and which have an advantageous balance of properties, such as in particular degree of curing and chemical stability.

SUMMARY OF THE INVENTION

The present invention relates to compounds of formula (I) according to patent claim 1, which are suitable as a one-component adhesive system/coating system for the improved coating, adhesive bonding and/or sealing of various substrate materials, such as, for example, metal, wood, glass and/or plastics material.

In the final cured state, the invention provides polymers condensed via —Si—O—Si— bridges as permanent coatings, adhesives and/or sealing materials.

The present invention further provides processes for the preparation of the compounds of formula (I) and of formula (IV).

DETAILED DESCRIPTION OF THE INVENTION

According to the invention there are provided compounds of formula (I):

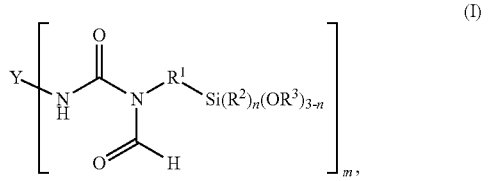

wherein in formula (I):
- Y represents an m-valent molecular radical which is a structural unit reduced by m NCO radicals of a monoisocyanate (m=1), of a polyisocyanate (m>1) or of an isocyanate-group-containing prepolymer (m=from 1 to 20);
- $R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;
- $R^2$ and $R^3$ each independently of the other represents an optionally substituted, linear or branched, aliphatic group having from 1 to 12 carbon atoms;
- n represents an integer from 0 to 2; and
- m represents a number from 1 to 20.

In one embodiment according to the invention, compounds of formula (I) are consequently provided.

In a further embodiment according to the invention there is provided a process for the preparation of the compound of formula (I), comprising reacting the silane-modified formamide of formula (Ia) with the isocyanate of the formula $Y—(NCO)_m$:

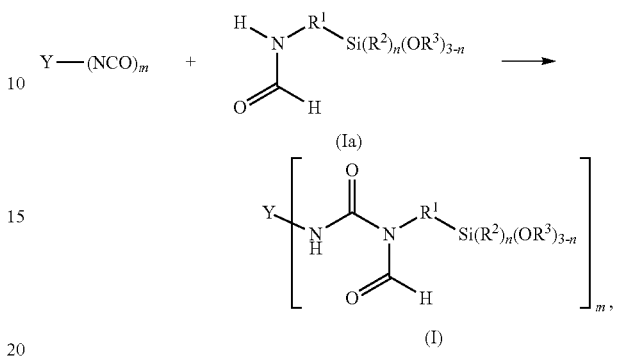

wherein Y, $R^2$, $R^3$, n and m are as defined in claim 1.

In a further embodiment according to the invention there is provided a reactive one-component adhesive system and/or coating system comprising at least one compound of formula (I).

According to the invention, the compound of formula (I) is used for the production of adhesives and sealing materials, lacquers, coatings, sizes, inks and/or printing inks.

In a further embodiment according to the invention there is described the use of the reactive one-component adhesive system according to the invention for the adhesive bonding and/or sealing of metal, wood, wood-based materials, glass, leather, textiles, plastics materials, mineral materials, cork, fibres, concrete, paper, cardboard and films.

There is additionally disclosed according to the invention a composite that is bonded by the one-component adhesive system according to the invention.

Definitions

As used in this application, the term "alicyclic" is to denote carbocyclic or heterocyclic compounds which do not belong to the aromatic compounds, such as, for example, cycloalkanes, cycloalkenes or oxa-, thia-, aza- or thiazacycloalkanes. Specific examples thereof are cyclohexyl groups, cyclopentyl groups and also derivatives thereof interrupted by one or two N or O atoms, such as, for example, pyrimidine, pyrazine, tetrahydropyran or tetrahydrofuran.

As used in this application, the term "araliphatic" is to denote alkyl radicals substituted by aryl groups, such as, for example, benzyl, phenylethyl, biphenyl, etc.

As used in this application, the expression "optionally substituted" or "substituted" is to denote in particular the substitution of the relevant structural unit by —F, —Cl, —I, —Br, —OH, —OCH$_3$, —OCH$_2$CH$_3$, —O-n-propyl or —O-isopropyl, —OCF$_3$, —CF$_3$, —S—C$_{1-6}$-alkyl and/or another linear or branched, aliphatic, alicyclic, araliphatic and/or aromatic structural unit having from 1 to 12 carbon atoms that is optionally linked via a heteroatom. Preferably, it denotes substitution by halogen (in particular —F, —Cl), C$_{1-6}$-alkoxy (in particular methoxy and ethoxy), hydroxy, trifluoromethyl and trifluoromethoxy.

As used in this application, the expression "low molecular weight" is to denote compounds whose molecular mass does not exceed approximately 800 g·mol$^{-1}$.

As used in this application, the expression "high molecular weight" is to denote compounds whose molecular mass exceeds approximately 800 g·mol$^{-1}$.

In the case of compounds whose molecular mass does not follow from an exactly defined structural formula, such as, for example, in the case of polymers, the molecular mass is to be understood as being the weight-average molecular weight in each case.

As used in this application, the term "monoisocyanate" is to denote a compound which is represented by A-NCO, wherein A represents an aromatic, araliphatic, aliphatic or cycloaliphatic group having from 6 to 50 carbon atoms.

As used in this application, the term "polyisocyanate" is to denote aromatic, araliphatic, aliphatic or cycloaliphatic polyisocyanates having an NCO functionality of preferably ≥2, in particular di- and tri-isocyanates.

As used in this application, the term "monomer" is to denote a low molecular weight compound with functional groups which is involved in the synthesis of oligomers and/or (pre)polymers and has a defined molar mass.

As used in this application, the term "oligomer" is to denote a compound in which only a few monomers of the same type or of different types are linked repeatedly to one another.

As used in this application, the term "prepolymer" is to denote oligomeric compounds with functional groups which are involved in the final synthesis of polymers.

As used in this application, the term "polymer" is to denote high molecular weight compounds in which monomers, oligomers and/or prepolymers of the same type or of different types are linked repeatedly to one another and which can differ in terms of degree of polymerisation, molar mass distribution or chain length.

Embodiments According to the Invention

Embodiments according to the invention are described in detail hereinbelow.

Compounds of Formula (I)

In one embodiment there are provided the compounds of the general formula (I):

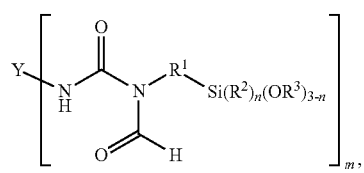

wherein in formula (I):
Y represents an m-valent molecular radical which is a structural unit reduced by m NCO radicals of a monoisocyanate (m=1), of a polyisocyanate (m>1) or of an isocyanate-group-containing prepolymer (m≥1);
$R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;
$R^2$ and $R^3$ each independently of the other represents an optionally substituted, linear or branched, aliphatic group having from 1 to 12 carbon atoms;
n represents an integer from 0 to 2; and
m represents a number from 1 to 20, wherein m can also be a fraction.

In one embodiment according to the invention, the structural unit Y is a radical derived from a monoisocyanate. Examples of such monoisocyanates are hexyl isocyanate, 6-chlorohexyl isocyanate, n-octyl isocyanate, cyclohexyl isocyanate, 2-ethylhexyl isocyanate, 2,3,4-methylcyclohexyl isocyanate, 3,3,5-trimethylcyclohexyl isocyanate, 2-norbornyl-methyl isocyanate, decyl isocyanate, dodecyl isocyanate, tetradecyl isocyanate, hexadecyl isocyanate, octadecyl isocyanate, 3-butoxypropyl isocyanate, 3-(2-ethylhexyloxy)-propyl isocyanate, phenyl isocyanate, tolyl isocyanates, chlorophenyl isocyanates (2,3,4-isomers), dichlorophenyl isocyanates, 4-nitrophenyl isocyanate, 3-trifluoromethylphenyl isocyanate, benzyl isocyanate, dimethylphenyl isocyanates (commercial mixture and individual isomers), 4-dodecylphenyl isocyanate, 4-cyclohexyl-phenyl isocyanate, 1-naphthyl isocyanate, isocyanato-amides of 1 mol of diisocyanates and 1 mol of monocarboxylic acids, preferably of toluene diisocyanates, diphenylmethane diisocyanates and hexamethylene diisocyanate with aliphatic monocarboxylic acids having preferably at least 6 carbon atoms, for example (6-isocyanato-hexyl)-stearic acid amide, (3-isocyanatotolyl)-stearic acid amide, (6-isocyanatohexyl)-benzamide, in each case on their own or in a mixture with a plurality of monoisocyanates.

In a further embodiment according to the invention, the structural unit Y is a radical derived from a polyisocyanate. There are used as suitable polyisocyanates the aromatic, araliphatic, aliphatic or cycloaliphatic polyisocyanates having an NCO functionality of preferably ≥2 that are known per se to the person skilled in the art. These can also have iminooxadiazinedione, isocyanurate, uretdione, urethane, allophanate, biuret, urea, oxadiazinetrione, oxazolidinone; acylurea and/or carbodiimide structures.

The polyisocyanates mentioned above are based on di- or tri-isocyanates having aliphatically, cycloaliphatically, araliphatically and/or aromatically bonded isocyanate groups that are known per se to the person skilled in the art, it being unimportant whether they have been prepared using phosgene or by phosgene-free processes. Examples of such di- and tri-isocyanates are 1,4-diisocyanatobutane, 1,5-diisocyanatopentane, 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis-(isocyanatomethyl)-cyclohexane, 1-isocyanato-3,3,5-trimethyl-5-isocyanatomethylcyclohexane (isophorone diisocyanate, IPDI), 4,4'-diisocyanatodicyclohexylmethane (Desmodur® W, Bayer AG, Leverkusen, DE), 4-isocyanatomethyl-1,8-octane diisocyanate (triisocyanatononane, TIN), diisocyanato-1,3-dimethylcyclohexane (H6XDI), 1-isocyanato-1-methyl-3-isocyanatomethylcyclohexane, 1-isocyanato-1-methyl-4-isocyanatomethylcyclohexane, bis-(isocyanatomethyl)-norbornane, 1,5-naphthalene diisocyanate, 1,3- and 1,4-bis-(2-isocyanato-prop-2-yl)-benzene (TMXDI), 2,4- and 2,6-diisocyanatotoluene (TDI), in particular the 2,4- and the 2,6-isomer and commercial mixtures of the two isomers, 2,4'- and 4,4'-diisocyanatodiphenylmethane (MDI), 1,5-diisocyanatonaphthalene, 1,3-bis(isocyanatomethyl)benzene (XDI) and arbitrary mixtures of mentioned compounds.

Particularly preferably, the polyisocyanates have a mean NCO functionality of from 2.0 to 5.0, most particularly preferably from 2.3 to 4.5, and a content of isocyanate groups of preferably from 5.0 to 27.0 wt. %, particularly preferably from 14.0 to 24.0 wt. %, and a content of monomeric diisocyanates of preferably less than 1 wt. %, particularly preferably less than 0.5 wt. %.

There are preferably used polyisocyanates or polyisocyanate mixtures of the above-mentioned type with solely aliphatically and/or cycloaliphatically bonded isocyanate groups.

Particularly preferably, the polyisocyanates of the above-mentioned type are based on hexamethylene diisocyanate, isophorone diisocyanate, the isomeric bis-(4,4'-isocyanatocyclohexyl)-methanes, TDI, MDI and mixtures thereof.

In a further embodiment according to the invention, the structural unit Y is a radical derived from a prepolymer carrying isocyanate groups. This can in particular be a polyurethane prepolymer. The preparation according to the invention of the polyurethane prepolymer carrying isocyanate groups Y—(NCO)$_m$ comprises the reaction of:
one or more polyisocyanates already mentioned
with
one or more polyols.

There can be used as suitable polyols all polyols known per se to the person skilled in the art from polyurethane chemistry, which polyols preferably have a mean OH functionality of ≥1.5, particularly preferably of from 1.8 to 2.5.

They can be, for example, low molecular weight diols (e.g. 1,2-ethanediol, 1,3- or 1,2-propanediol, 1,4-butanediol, 2,2,4-trimethylpentanediol), triols (e.g. glycerol, trimethylolpropane) and tetraols (e.g. pentaerythritol), polyether polyols, polyester polyols, polyacrylate polyols as well as polycarbonate polyols. Preferred polyols are substances of the above-mentioned type based on polyethers.

When polyether polyols are used, polyether polyols having a number-average molecular weight Mn of preferably from 300 to 20,000 g/mol, particularly preferably from 1000 to 12,000 g/mol, most particularly preferably from 2000 to 6000 g/mol, are used.

Furthermore, they preferably have a mean OH functionality of ≥1.9, particularly preferably ≥1.95.

The OH functionality of these polyethers is preferably <6, particularly preferably <4, most particularly preferably <2.2.

Polyols that are likewise suitable are polyester polyols from the condensation reaction of suitable alcohols and acids. There are used as alcohols primary and diprimary diols, such as ethylene glycol, diethylene glycol, triethylene glycol, 1,2-propylene glycol, dipropylene glycol, 1,3-butanediol, 1,4-butanediol, 1,6-hexanediol or neopentyl glycol, as well as higher-hydric alcohols, such as trimethylolpropane, trimethylolethane or pentaerythritol. Suitable condensation partners are acid components such as adipic acid or phthalic acids. The ring-opening polymerisation of ε-caprolactone or methyl-ε-caprolactone using metal catalysts such as, for example, Sn(II) ethylhexanoate or titanium tetraalkoxylates and diols or triols of the above-mentioned type as starters also yields suitable polyester polyols. The length of the polyester polyol can thereby be determined by the number of caprolactone units used.

The preferred molecular weight of the polyester polyols (number average) is ≤1000 g/mol. The preferred functionality of the polyester polyols is from 2 to 3.

Polyacrylate polyols are also suitable for the preparation of the prepolymers according to the invention. The polyacrylate polyols have a number-average molecular weight of from 200 to 10,000 g/mol, particularly preferably from 200 to 6000 g/mol and most particularly preferably from 200 to 2500 g/mol. The functionality of the polyacrylate polyols used is preferably from 1.6 to 3.8, particularly preferably from 1.8 to 3.5. The OH number of these polyacrylate polyols is preferably from 15 to 150, particularly preferably from 20 to 100 and most particularly preferably from 40 to 80 mg KOH/g. Acryflow® P60 and P90 (commercial products from Lyondell, US), for example, are suitable.

Aliphatic polycarbonate polyols also come into consideration for the synthesis of the prepolymers according to the invention. Polycarbonate polyols can be obtained, as is known, from the condensation reaction of phosgene with polyols or from the transesterification of suitable organic carbonates with polyols. There come into consideration as organic carbonates aryl, alkyl and alkylene carbonates and mixtures thereof. Examples which may be mentioned are diphenyl carbonate (DPC), dimethyl carbonate (DMC), diethyl carbonate (DEC) and ethylene carbonate. There come into consideration as polyols the polyols mentioned above under the section polyester polyols. The functionality of the polycarbonate polyols used is preferably from 1.6 to 3.8, particularly preferably from 1.8 to 3.5. These polycarbonate polyols have a number-average molar weight of preferably from 100 to 6000 g/mol and particularly preferably from 100 to 4000 g/mol. The OH number is dependent on the functionality of the polycarbonate polyols and is typically from 20 to 900 mg KOH/g.

Further suitable polyols are, for example, also the specific polyols described in EP-A 0 689 556 and EP-A 0 937 110, for example obtainable by reaction of epoxidised fatty acid esters with aliphatic or aromatic polyols with epoxide ring opening.

Hydroxyl-group-containing polybutadienes can likewise be used as polyols.

The preparation of the polyurethane prepolymers Y—(NCO)$_m$ according to the invention is carried out in principle in the manner known from polyurethane chemistry. The polyols (individually or in the form of a mixture) are thereby reacted with an excess of the polyisocyanate (individually or in the form of a mixture), optionally in the presence of a catalyst and/or of auxiliary substances and additives. The homogeneous reaction mixture is stirred until a constant NCO value is reached. Any unreacted polyisocyanate can then be removed by continuous distillation.

A continuous distillation process within the meaning of the invention is understood as being a process in which only a partial amount of the prepolymer from the above-described process step is briefly exposed to an elevated temperature, while the amount that is not yet in the distillation process remains at a significantly lower temperature. An elevated temperature is to be understood as being the temperature for evaporation of the volatile constituents at a correspondingly chosen pressure.

The distillation is preferably carried out at a temperature of less than 170° C., particularly preferably from 110 to 170° C., most particularly preferably from 125 to 145° C., and at pressures of less than 20 mbar, particularly preferably less than 10 mbar, most particularly preferably at from 0.05 to 5 mbar.

The temperature of the amount of the prepolymer-containing reaction mixture that is not yet in the distillation process is preferably from 0 to 60° C., particularly preferably from 15 to 40° C. and most particularly preferably from 20 to 40° C.

In a preferred embodiment of the invention, the temperature difference between the distillation temperature and the temperature of the amount of the prepolymer-containing reaction mixture that is not yet in the distillation process is at least 5° C., particularly preferably at least 15° C., most particularly preferably from 15 to 40° C.

The distillation is preferably carried out at a rate such that a volume increment of the prepolymer-containing reaction mixture that is to be distilled is exposed to the distillation temperature for less than 10 minutes, particularly preferably for less than 5 minutes, and is then returned to the starting temperature of the prepolymer-containing reaction mixture prior to the distillation optionally by active cooling. The temperature load is preferably such that the temperature of the reaction mixture before the distillation, or of the prepolymer after the distillation, is at least 5° C., particularly preferably at least 15° C., most particularly preferably from 15 to 40° C., higher than the applied distillation temperature.

Preferred continuous distillation techniques are molecular, falling-film and/or film distillation (see in this connection, for example, Chemische Technik, Wiley-VCH, Volume 1, 5th edition, pages 333-334).

Falling-film evaporators consist of a stationary bundle of long tubes into which the liquid to be evaporated is introduced at the top and flows downwards as a film. Heating takes place in the shell by means of steam. Vapour bubbles form in the tubes and flow downwards with the liquid and ensure turbulent conditions. The vapour and the liquid are separated at the bottom end in a separator vessel.

Film evaporators are suitable apparatuses for the evaporation of temperature-sensitive substances which may be exposed to heat for only a short time. The liquid to be evaporated is introduced at the top into a tube with jacket heating. It flows downwards in the tube as a film. Inside the tube, a wiper suspended on a shaft rotates and ensures a constant film thickness. Film distillation with the parameters mentioned above is preferably used as the continuous distillation technique.

The equivalent ratio of the NCO groups of the polyisocyanate to the OH groups of the polyol in the reaction is preferably from 10:1 to 2:1, particularly preferably from 7:1 to 2:1.

The chosen reaction temperature is from 0° C. to 250° C., preferably from 20° C. to 140° C., most particularly preferably from 40° C. to 100° C.

The process according to the invention can naturally also be carried out in the presence of solvents such as aromatic compounds, chlorinated aromatic compounds, esters or chlorinated hydrocarbons.

In order to accelerate the urethanisation it is possible to use catalysts known per se, such as organometallic compounds, amines (e.g. tertiary amines) or metal compounds such as lead octoate, mercury succinate, zinc triflate, tin octoate or dibutyltin dilaurate. If catalysts are used concomitantly, they are preferably added in amounts of from 0.001 to 5 wt. %, in particular from 0.002 to 2 wt. %, based on the total amount of the polyisocyanates and polyols that are to be reacted.

Preferred Substituent Meanings in Formulae (I) and (III)

There are preferably provided compounds of formulae (I) and (III) wherein in each case:
R represents methylene (—$CH_2$—), ethylene (—$CH_2CH_2$—), propylene (—$CH_2CH_2CH_2$—), isophorylene, 4,4'-dicyclohexylmethylene, bis(cyclohexylene), 4,4'-bisphenylene, o-, m- or p-tolylene, or hexylene (in particular —$CH_2CH_2CH_2CH_2CH_2CH_2$—), and particularly preferably n-hexylene;
$R^1$ represents methylene (—$CH_2$—) or propylene (in particular n-propylene —$CH_2CH_2CH_2$—), particularly preferably n-propylene;
$R^2$ and $R^3$ each independently of the other represents methyl or ethyl, preferably ethyl; and
n represents an integer from 0 to 2.

There are particularly preferably provided compounds of formula (I) and/or (III) wherein in each case:
R represents isophorylene, 4,4'-dicyclohexylmethylene, bis(cyclohexylene), bisphenylene, tolylene or n-hexylene;
$R^1$ represents n-propylene;
$R^2$ and $R^3$ each independently of the other represents methyl or ethyl; and
n represents an integer from 0 to 2.

There are most particularly preferably provided compounds of formula (III) wherein R is isophorylene, tolylene or n-hexylene, $R^1$ is n-propylene, $R^2$ and $R^3$ are methyl and n=0.

The compounds of formula (I) according to the invention are suitable as binders for coating materials, adhesives and/or sealing materials.

The compounds of formula (I) have viscosities (at 23° C.) in the range of from 100 to 1,000,000 mPa·s, preferably from 1000 to 500,000 mPa·s, particularly preferably from 5000 to 300,000 mPa·s.

On account of the acylurea group that is present, the compounds of formula (I) according to the invention are of lower viscosity as compared with analogous products containing a urea group. This results, as is known to the person skilled in the art, in improved manageability or further processing to pigmented coatings or in better incorporation of fillers such as, for example, chalks for the formulation of adhesives or sealing materials.

Process for the Preparation of the Compounds of Formula (I)

The compounds of formula (I) according to the invention can be prepared by the following two-stage process:

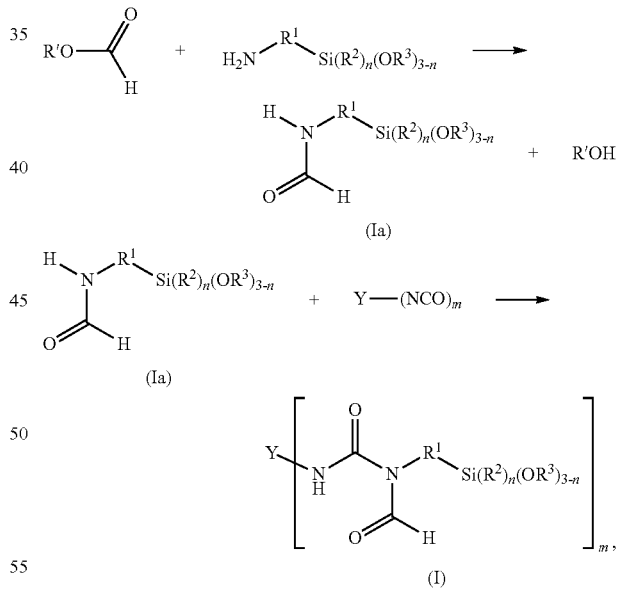

An excess of the formic acid alkyl ester R'O—CHO is preferably first added dropwise to the amine $H_2N$—$R^1$—Si$(R^2)_n(OR^3)_{3-n}$, R' preferably representing an alkyl group having from 1 to 4 carbon atoms. Methyl formate or ethyl formate is particularly preferred as the formic acid alkyl ester R'O—CHO. Preferably, 1 mol of amine is reacted with an excess of from 1.01 to 6 mol of formic acid alkyl ester R'O—CHO, particularly preferably from 1.05 to 4 mol, at the boiling temperature of the formic acid alkyl. When the reaction is complete, excess formic acid alkyl ester R'O—

CHO and the resulting alcohol R'—OH are distilled off by means of film distillation and the resulting product (Ia) is optionally filtered off.

The compound of formula (Ia) is then reacted with Y—(NCO)$_m$, preferably under inert conditions, at temperatures of from 20 to 200° C., preferably from 40 to 160° C. The two components are thereby used in an equivalent ratio of isocyanate groups to formamide groups of from at least 1:10 to not more than 40:1, preferably from 1:5 to not more than 30:1 and particularly preferably from 1:2 to not more than 25:1. The reaction can be carried out in solution or solvent-free.

The preparation of the compounds having the formula (I) can be carried out without the use of catalysts. However, known catalysts can optionally also be added in order to accelerate the reaction. There can be used, for example, tertiary amities, such as, for example, triethylamine, tributylamine, dimethylbenzylamine, diethylbenzylamine, pyridine, methylpyridine, dicyclohexylmethylamine, dimethylcyclohexylamine, N,N,N',N'-tetramethyldiaminodiethyl ether, bis-(dimethylaminopropyl)-urea, N-methyl- or N-ethyl-morpholine, N-cocomorpholine, N-cyclohexylmorpholine, N,N,N',N'-tetramethylethylenediamine, N,N,N',N'-tetramethyl-1,3-butanediamine, N,N,N',N'-tetramethyl-1,6-hexanediamine, pentamethyldiethylenetriamine, N-methylpiperidine, N-dimethyl-aminoethylpiperidine, N,N'-dimethylpiperazine, N-methyl-N'-dimethylaminopiperazine, 1,2-dimethylimidazole, 2-methylimidazole, N,N-dimethylimidazole-β-phenylethylamine, 1,4-diazabicyclo-(2,2,2)-octane (DABCO) and bis-(N,N-dimethylaminoethyl) adipate, amidines, such as, for example, 1,5-diazabicyclo[4.3.0]nonene (DBN), 1,8-diazabicyclo(5.4.0)undec-7-ene (DBU) and 2,3-dimethyl-3,4,5,6-tetrahydropyrimidine, alkanolamine compounds, such as, for example, triethanolamine, triisopropanolamine, N-methyldiethanolamine, N-ethyl-diethanolamine, dimethylaminoethanol and 2-(N,N-dimethylaminoethoxy)ethanol, N,N', N"-tris-(dialkylaminoalkyl)hexahydrotriazines, such as, for example, N,N',N"-tris-(dimethylaminopropyl)-s-hexahydrotriazine, bis(dimethylaminoethyl) ether and also metal salts, such as, for example, inorganic and/or organic compounds of iron, lead, bismuth, zinc and/or tin in conventional oxidation states of the metal, for example iron(II) chloride, iron(III) chloride, bismuth(III) 2-ethylhexanoate, bismuth (III) octoate, bismuth(III) neodecanoate, zinc chloride, zinc 2-ethylcaproate, zinc(II) trifluoromethanesulfonate (zinc triflate), tin(II) octoate, tin(II) ethylcaproate, tin(II) palmitate, dibutyltin(IV) dilaurate (DBTL), dibutyltin(IV) dichloride or lead octoate.

Preferred catalysts that are to be used are tertiary amines, amidines and tin compounds or zinc compounds of the mentioned type. Particularly preferred catalysts are 1,4-diazabicyclo-(2,2,2)-octane (DABCO), 1,5-diazabicyclo [4.3.0]nonene (DBN), 1,8-diazabicyclo(5.4.0)undec-7-ene (DBU) as well as dibutyltin(IV) dilaurate (DBTL) and zinc(II) trifluoromethanesulfonate (zinc triflate).

The catalysts mentioned by way of example above can be used in the reaction individually or in the form of arbitrary mixtures and are employed, if at all, in amounts of from 0.001 to 1.0 wt. %, preferably from 0.01 to 0.5 wt. %, calculated as the total amount of catalysts used, based on the total amount of starting compounds used.

The progress of the reaction can be monitored, for example, by determining the NCO content by titrimetry. When the desired NCO content has been reached, the reaction is terminated.

The compounds of formula (I) prepared in that manner are clear, virtually colourless products which, depending on the chosen starting materials, are low- to high-viscosity liquids and have residual contents of monomeric starting diisocyanates of less than 1.0 wt. %, preferably of less than 0.5 wt. %, particularly preferably of less than 0.3 wt. %, based on the total mass of the reaction product.

Any residual NCO contents that are still detectable can be taken up by addition of methanol.

In order to prevent premature crosslinking of the silane groups of the compounds of formula (I) during the preparation according to the invention, it can be advantageous to add water acceptors. For example, there can be used orthoformic esters, such as, for example, triethyl orthoformate, vinylsilanes, such as, for example, vinyltrimethoxysilane, or organic phosphates, such as, for example, dibutyl phosphate. The water acceptors are used, if necessary, in amounts of up to 5 wt. %, preferably up to 2 wt. %, based on the total amount of starting materials.

If catalysts and/or water acceptors are used, they can be added to the starting compounds before the start of the actual reaction. It is, however, also possible to add these auxiliary substances to the reaction mixture at any desired point in time during the reaction.

In a preferred embodiment, the processes described herein take place under a protecting gas atmosphere, such as, for example, nitrogen.

The silane-modified polymers of formula (I) disclosed herein can be used according to the invention for the production of adhesives and sealing materials, lacquers, coatings, sizes, inks and/or printing inks.

The advantage of this process is that the properties of the silane-modified polymers of formula (I) can be adapted to a large number of very different applications via the structures of the formula Y—(NCO)$_m$ that are used.

Reactive One-Component Adhesive System

According to the invention, the compounds of formula (I) are used for a reactive one-component adhesive system. The reactive one-component adhesive system is characterised in that it comprises at least one compound of formula (I).

Under the action of moisture or water, hydrolysis of the hydrolysable radicals of the silane groups takes place, followed by crosslinking (curing) of the silanols formed thereby, with cleavage of water.

Catalysts that accelerate the hydrolysis and condensation of the silanol groups can also be used concomitantly. Such catalysts are known to a person skilled in the art. There can be used, for example, acids, such as, for example, sulfuric acid, p-toluenesulfonic acid, trifluoromethane-sulfonic acid, acetic acid, trifluoroacetic acid and dibutyl phosphate, bases, such as, for example, N-substituted amidines, such as 1,5-diazabicyclo[4.3.0]non-5-ene (DBN) and 1,5-diazabicyclo-[5.4.0]undec-7-ene (DBU), but also metal salts and metal dictates, such as, for example, tetraisopropyl titanate, tetrabutyl titanate, titanium(IV) acetylacetonate, aluminium tri-sec-butylate, aluminium acetylacetonate, aluminium triflate or tin triflate.

These catalysts are used, if at all, in amounts of up to 5 wt. %, preferably up to 2 wt. %, based on the weight of the silane-modified prepolymers that are used. Depending on the nature and amount of the catalyst used, curing of the one-component adhesive system formulated from the compounds of formula (I) according to the invention can take place over a wide temperature range, for example from −20 to 200° C., preferably from 0 to 180° C., particularly preferably from 20 to 160° C.

There can optionally be added to the reactive one-component adhesive system according to the invention as reaction partners also any desired further hydrolysable silane compounds, such as, for example, tetramethoxysilane, tetraethoxysilane, methyltrimethoxysilane, methyltriethoxysilane, ethyltriethoxysilane, isobutyltrimethoxysilane, isobutyltriethoxysilane, octyltriethoxysilane, octyltrimethoxysilane, (3-glycidyloxypropyl)-methyldiethoxysilane, (3-glycidyloxypropyl)-trimethoxysilane, phenyltrimethoxysilane, phenyltriethoxysilane or silane-functional copolymers of the type mentioned in U.S. Pat. No. 4,499,150, or mixtures of such silane compounds.

The reactive one-component adhesive system of the invention can likewise optionally comprise further additives and/or auxiliary substances which are known in the prior art. Mention may be made of, for example, pigments, antioxidants, water acceptors, fillers, slip additives, flow agents, rheology additives, foam stabilisers, hydrophobising agents, air void formers, adhesion-enhancing additives (adhesion promoters), compounding agents, plasticisers, anti-ageing agents, flame retardants and/or UV stabilisers.

There may be mentioned as suitable fillers, for example, carbon black, precipitated silicas, pyrogenic silicas, mineral chalks and precipitated chalks. Examples of suitable plasticisers which may be mentioned are phthalic acid esters, adipic acid esters, alkylsulfonic acid esters of phenol, phosphoric acid esters or also higher molecular weight polypropylene glycols.

There may be mentioned as water acceptors in particular alkoxysilyl compounds such as vinyltrimethoxysilane, methyltrimethoxysilane, isobutyltrimethoxysilane, hexadecyltrimethoxysilane.

There are used as adhesion promoters the known functional silanes such as, for example, aminosilanes of the type mentioned above, but also N-aminoethyl-3-aminopropyl-trimethoxy- and/or N-aminoethyl-3-aminopropylmethyl-dimethoxy-silane, epoxysilanes and/or mercaptosilanes.

As well as being used as a one-component adhesive system, the compounds of formula (I) according to the invention can also be added to conventional one-component and/or two-component polyurethane adhesive systems, for example as an additive.

If the reactive one-component adhesive system according to the invention, as described above, is applied beforehand to the substrates that are to be bonded, permanent bonding or sealing of the substrates occurs as a result of the above-described crosslinking.

It may be necessary for the surfaces of the substrates that are to be bonded to be pretreated by a physical, chemical and/or physical-chemical process. The application of a primer or of an adhesion promoter composition, for example, is advantageous here but is not absolutely necessary according to the invention. It can therefore also be omitted in one embodiment.

Substrates

Suitable substrates which are suitable for adhesive bonding and/or sealing by means of the reactive one-component adhesive system according to the invention are metals, glass, wood, concrete, stone, ceramics, textiles and/or plastics materials. The substrates that are to be bonded can be the same or different.

In a preferred embodiment, the reactive one-component adhesive system according to the invention is used for the adhesive bonding and/or sealing of metals, glass and/or plastics materials.

Suitable metal substrates can generally be produced from all metals or metal alloys that are conventional in the field. Metals such as, for example, aluminium, stainless steel, steel, titanium, iron-containing metals and alloys are preferably used. The substrates that are to be bonded can additionally be composed of different metals.

The plastics substrates that are to be bonded are, for example, polycarbonates (PC), polyamides, polyvinyl chloride, polyurethanes, polyvinyl acetate, polyacrylates or polymethacrylates, polyethylene, polystyrene, polypropylene and/or polyesters, such as, for example, polybutylene terephthalate (PBT) and/or polyethylene terephthalate (PET).

The substrates can additionally be lacquered or printed.

The substrates that are to be bonded can further have any desired form necessary for the use of the resulting composite. In the simplest form, the substrates are planar. Three-dimensional substrates can, however, also be bonded using the reactive one-component adhesive system according to the invention.

Composite

There is likewise provided according to the invention a composite that is bonded by the reactive one-component adhesive system according to the invention, as defined above.

EXPERIMENTAL PART

The examples which follow serve to illustrate the present invention but are not to be interpreted as being a limitation of the scope of protection.

All percentages relate to weight, unless specified otherwise.

The NCO contents were determined titrimetrically in accordance with DIN EN ISO 11909.

OH numbers were determined titrimetrically in accordance with DIN 53240-2: 2007-11, and acid numbers were determined in accordance with DIN 3682 5. The indicated OH contents were calculated from the analytically determined OH numbers.

The residual monomer contents were measured in accordance with DIN EN ISO 10283 by gas chromatography with an internal standard.

Molecular weights were determined by gel permeation chromatography in accordance with DIN 55672-1 (Gel permeation chromatography (GPC)—Part 1: Tetrahydrofuran (THF) as eluant) against polystyrene standards, with the difference that a flow rate of 0.6 ml/min instead of 1.0 ml/min was used.

All viscosity measurements were carried out using a Physica MCR 51 rheometer from Anton Paar Germany GmbH (DE) in accordance with DIN EN ISO 3219.

Synthesis of Silane-Modified Formamides Having the Formula (Ia)

Example 1: N-(3-Trimethoxysilylpropyl)Formamide 1075.8 g (6 mol) of 3-aminopropyltrimethoxysilane are placed at room temperature, under a nitrogen atmosphere, in a flask having a thermometer, a KPG stirrer, a reflux condenser and a dropping funnel. 378.6 g (6.3 mol) of methyl formate are added dropwise, with stirring, in such a manner that the temperature does not exceed 50° C. When the exothermic reaction has subsided, stirring is continued for 4 hours at room temperature, and then excess methyl formate and the resulting methyl alcohol are distilled off under reduced pressure (0.1 mbar at 50° C.). A colourless liquid having a viscosity of 11 mPa·s at 23° C. is obtained.

Example 2:
N-(3-Methyldimethoxysilylpropyl)Formamide 99.6 g (0.6 mol) of 3-aminopropylmethyldimethoxysilane are placed at room temperature, under a nitrogen atmosphere, in a flask having a thermometer, a KPG stirrer, a reflux condenser and a dropping funnel. 40.3 g (0.67 mol) of methyl formate are added dropwise, with stirring, in such a manner that the temperature does not exceed 50° C. When the exothermic reaction has subsided, stirring is continued for 4 hours at room temperature, and then excess methyl formate and the resulting methyl alcohol are distilled off under reduced pressure (0.1 mbar at 50° C.). A colourless liquid is obtained.

Example 3: N-(3-Triethoxysilylpropyl)Formamide 221.4 g (1 mol) of 3-aminopropyltriethoxysilane are placed at room temperature, under a nitrogen atmosphere, in a flask having a thermometer, a KPG stirrer, a reflux condenser and a dropping funnel. 77.8 g (1.05 mol) of ethyl formate are added dropwise, with stirring, in such a manner that the temperature does not exceed 50° C. When the exothermic reaction has subsided, stirring is continued for 4 hours at room temperature, and then excess ethyl formate and the resulting ethyl alcohol are distilled off under reduced pressure (0.1 mbar at 80° C.). A colourless liquid having a viscosity of 13 mPa·s at 23° C. is obtained.

Example 4:
N-(3-Methyldiethoxysilylpropyl)Formamide 497.9 g (2.6 mol) of 3-aminopropylmethyldiethoxysilane are placed at room temperature, under a nitrogen atmosphere, in a flask having a thermometer, a KPG stirrer, a reflux condenser and a dropping funnel. 212.1 g (2.8 mol) of ethyl formate are added dropwise, with stirring, in such a manner that the temperature does not exceed 50° C. When the exothermic reaction has subsided, stirring is continued for 4 hours at room temperature, and then excess ethyl formate and the resulting ethyl alcohol are distilled off under reduced pressure (0.1 mbar at 80° C.). A colourless liquid having a viscosity of 12 mPas at 23° C. is obtained.

Synthesis of Silane-Modified Compounds Having the General Formula (I)

Example 5

154.5 g (0.915 mol) of HDI and 25 mg (30 ppm) of zinc(II) triflate are placed at 60° C., under a nitrogen atmosphere, in a flask having a thermometer, a KPG stirrer, a reflux condenser and a dropping funnel. 469.5 g of a polypropylene glycol (OH number: 112 mg KOH/g) and 201 g of a polyether (OH number: 52 mg KOH/g) are then added dropwise. The reaction mixture is stirred at 60° C. until a constant isocyanate content (3.0 wt. %) is reached. 142.8 g (0.69 mol) of N-(3-trimethoxysilylpropyl)formamide (from Example 1) are then metered in, and the reaction mixture is stirred at 80° C. until no further isocyanate content is detectable by titrimetry. 32 mg of dibutyl phosphate are added to stabilise the resulting silane-terminated prepolymer, and 2.14 g of vinyltrimethoxysilane are added as water acceptor. The resulting binder is a clear colourless mass and has a viscosity of 21,000 mPa·s at 23° C.

Example 6: (Comparison Example to Example 5)

154.5 g (0.915 mol) of HDI and 25 mg (30 ppm) of DBTL (dibutyltin dilaurate) are placed at 60° C., under a nitrogen atmosphere, in a flask having a thermometer, a KPG stirrer, a reflux condenser and a dropping funnel. 469.5 g of a polypropylene glycol (OH number: 112 mg KOH/g) and 201 g of a polyether (OH number: 52 mg KOH/g) are then added dropwise. The reaction mixture is stirred at 60° C. until a constant isocyanate content (3.0 wt. %) is reached. 123.7 g (0.69 mol) of 3-aminopropyltrimethoxysilane are then metered in, and the reaction mixture is stirred at 80° C. until no further isocyanate content is detectable by titrimetry. 32 mg of dibutyl phosphate are added to stabilise the resulting silane-terminated prepolymer, and 2.14 g of vinyltrimethoxysilane are added as water acceptor. The resulting binder is a cloudy whitish mass and has a viscosity of 100,000 mPa·s at 23° C.

Example 7

519.0 g of Desmodur® N 75 BA (polyisocyanate (biuret based on HDI 75% in butyl acetate) from Bayer MaterialScience AG; isocyanate content 16.5 wt. %) are placed at 80° C. with 50 ppm of DABCO, under a nitrogen atmosphere, in a flask having a thermometer, a KPG stirrer, a reflux condenser and a dropping funnel. 518.0 g (2.8 mol) of N-(3-trimethoxysilylpropyl)formamide (from Example 1) are then added dropwise, with stirring. When the addition is complete, the reaction mixture is stirred at 80° C. until no further isocyanate content is detectable by titrimetry. The resulting binder has a viscosity of 6240 mPa·s at 23° C.

For further processing, the binder is adjusted to a solids content of 50% with butyl acetate, and 0.25% Lupragen® N 700 (1,8-diazabicyclo-5,4,0-undec-7-ene) from BASF is added; the whole is applied with a knife in a layer thickness (wet) of 50 μm to glass plates. After a drying time of 4 hours at 23° C. and a relative humidity of 50%, the coating is touch-dry and after 4 days exhibits good solvent resistance to xylene, 1-methoxy-2-propyl acetate, ethyl acetate and acetone.

Example 8

578.0 g of Desmodur® L75 (polyisocyanate based on TDI 75% in ethyl acetate) from Bayer MaterialScience AG; isocyanate content 13.3 wt. %) are placed at 80° C. with 50 ppm of DABCO, under a nitrogen atmosphere, in a flask having a thermometer, a KPG stirrer, a reflux condenser and a dropping funnel. 522.0 g (2.5 mol) of N-(3-trimethoxysilylpropyl)formamide (from Example 1) are added dropwise, with stirring. When the addition is complete, the reaction mixture is stirred at 80° C. until no further isocyanate content is detectable by titrimetry. The resulting binder has a viscosity of 92,000 mPa·s at 23° C.

For further processing, the binder is adjusted to a solids content of 50% with ethyl acetate, and 0.25% Lupragen® N 700 (1,8-diazabicyclo-5,4,0-undec-7-ene) from BASF SE is added; the whole is applied with a knife in a layer thickness (wet) of 50 μm to glass plates. After a drying time of 4 hours at 23° C. and a relative humidity of 50%, the coating is touch-dry and after 4 days exhibits good solvent resistance to xylene, 1-methoxy-2-propyl acetate, ethyl acetate and acetone.

Example 9

201.6 g (1.2 mol) of HDI are placed at 80° C., under a nitrogen atmosphere, in a flask having a thermometer, a KPG stirrer, a reflux condenser and a dropping funnel, and 87.6 g (0.6 mol) of 2,2,4-trimethylpentane-1,3-diol are added in portions. 346 g of butyl acetate as solvent and 52 mg of triethylamine as catalyst are then metered in. When a constant isocyanate content (8.2 wt. %) has been reached, 248.4 g (1.2 mol) of N-(3-trimethoxysilylpropyl)formamide (from Example 1) are added dropwise and the batch is stirred at 80° C. until no further isocyanate content is detectable by titrimetry. The resulting clear binder has a viscosity of 41 mPa·s at a solids content of 50%.

For further processing, 0.25% Lupragen® N 700 (1,8-diazabicyclo-5,4,0-undec-7-ene) from BASF SE is added to the binder, and the whole is applied with a knife in a layer thickness (wet) of 50 μm to glass plates. After a drying time of 4 hours at 23° C. and a relative humidity of 50%, the coating is touch-dry and after 4 days exhibits good solvent resistance to xylene, 1-methoxy-2-propyl acetate, ethyl acetate and acetone.

Example 10: (Comparison Example to Example 9)

201.6 g (1.2 mol) of HDI are placed at 80° C., under a nitrogen atmosphere, in a flask having a thermometer, a KPG stirrer, a reflux condenser and a dropping funnel, and 87.6 g (0.6 mol) of 2,2,4-trimethylpentane-1,3-diol are added in portions. 346 g of butyl acetate as solvent and 52 mg of triethylamine as catalyst are then metered in. When a constant isocyanate content (8.2 wt. %) has been reached, 215.1 g (1.2 mol) of 3-aminopropyltrimethoxysilane are added dropwise. Shortly after the beginning of the addition, the reaction mixture becomes cloudy and the batch solidifies at room temperature despite further dilution to a solids content of less than 50%. Further processing of the batch as a lacquer binder is not possible.

Application Examples for Adhesives and Sealing Materials

In order to assess the application properties of the prepolymer from Example 9, it is processed in the following formulation:

|  | Amount used in wt. % |
|---|---|
| Polymer | 31.34 |
| Filler (Socal U₁S₂) | 47.01 |
| Plasticiser (Jayflex DINP) | 18.80 |
| Drying agent (Dynasylan VTMO) | 1.88 |
| Adhesion promoter (Dynasylan 1146) | 0.94 |
| Catalyst (Lupragen N 700) | 0.03 |

In order to prepare the formulation, the filler (Socal® U1S2 from Solvay), the plasticiser (Jayflex™ DINP from Exxon) and the drying agent (Dynasylan® VTMO from Evonik) are added to the binder, and mixing is carried out at 3000 rpm in a vacuum dissolver with a wall scraper. The adhesion promoter (Dynasylan® 1146 from Evonik) is then added and incorporated by stirring in the course of 5 minutes at 1000 rpm. Lastly, the catalyst (Lupragen® N700 from BASF SE) is stirred in at 1000 rpm, and the finished mixture is finally exposed to the air in vacuo.

In order to measure the physical properties, both membranes having a thickness of 2 mm and test specimens on a glass substrate are prepared in accordance with DIN EN ISO 11600. Testing of the Shore hardness was carried out on the membranes in accordance with DIN 53505. The modulus at 50% elongation is measured in accordance with DIN EN ISO 11600 at 23° C.

The following results were obtained:

|  | Ex. 15 (prepolymer from Ex. 9) |
|---|---|
| Shore A hardness | 52 |
| 50% modulus [N/mm²] | 2.4 |
| Film drying time, 100 μm [min] | 150 |
| Elongation at break [%] | 64.6 |

The invention claimed is:

1. A compound of formula (I):

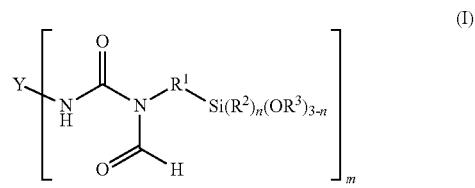

wherein in formula (I):

Y represents a m-valent molecular radical which is a structural unit reduced by m NCO radicals of a monoisocyanate (m=1), of a polyisocyanate (m>1) or of an isocyanate-group-containing prepolymer (m=from 1 to 20);

$R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;

$R^2$ and $R^3$ each independently of the other represents an optionally substituted, linear or branched, aliphatic group having from 1 to 12 carbon atoms;

n represents an integer from 0 to 2; and m represents a number from 1 to 20.

2. The compound according to claim 1, wherein $R^2$ and $R^3$ each independently of the other represents methyl or ethyl.

3. The compound according to claim 1, wherein Y represents a molecular radical which is a structural unit reduced by m NCO radicals of a monoisocyanate (m=1), of a polyisocyanate (m>1) or of an isocyanate-group-containing prepolymer (m=from 1 to 20), $R^1$ represents propyl, $R^2$ and $R^3$ each independently of the other represents methyl or ethyl, and n represents an integer from 0 to 2.

4. A process for the preparation of the compound of formula (I), comprising reacting a compound of formula (Ia) with a structural unit of the formula Y—(NCO)$_m$:

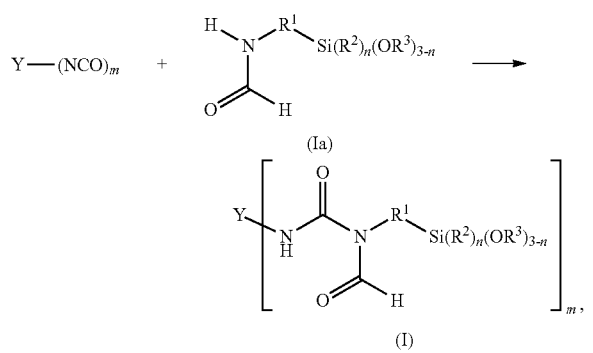

wherein Y, $R^1$, $R^2$, $R^3$, n and m are as defined in claim 1.

5. A method comprising utilizing the compound according to claim 1 for the production of adhesives and sealing materials, lacquers, coatings, sizes, inks and/or printing inks.

6. A reactive one-component adhesive system comprising at least one compound according to claim 1.

7. A method comprising utilizing the reactive one-component adhesive system according to claim 6 for the adhesive bonding and/or sealing of metal, wood, wood-based materials, glass, leather, textiles, plastics materials, mineral materials, cork, fibres, concrete, paper, cardboard or films.

8. A kit comprising the reactive one-component adhesive system according to claim 6, for the adhesive bonding and/or sealing of metal, wood, wood-based materials, glass, leather, textiles, plastics materials, mineral materials, cork, fibres, concrete, paper, cardboard or films.

9. Composite bonded by the reactive one-component adhesive system according to claim 6.

10. A reactive one-component coating system comprising at least one compound according to claim 1.

11. A method comprising utilizing the reactive one-component coating system according to claim 10 for the coating of metal, wood, wood-based materials, glass, leather, textiles, plastics materials, mineral materials, cork, fibres, concrete, paper, cardboard or films.

12. A kit comprising the reactive one-component coating system according to claim 10, for the coating of metal, wood, wood-based materials, glass, leather, textiles, plastics materials, mineral materials, cork, fibres, concrete, paper, cardboard or films.

13. A composite bonded by the reactive one-component coating system according to claim 10.

14. A compound of formula (I):

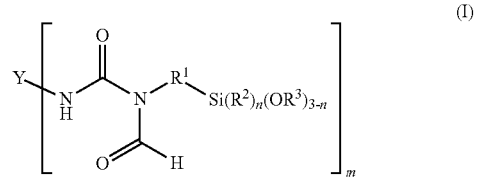

wherein in formula (I):
Y is a radical derived from a monoisocyanate, from a polyisocyanate, or from a prepolymer carrying isocyanate groups;
$R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;
$R^2$ and $R^3$ each independently of the other represents an optionally substituted, linear or branched, aliphatic group having from 1 to 12 carbon atoms;
n represents an integer from 0 to 2; and
m represents a number from 1 to 20.

15. The compound according to claim 14, wherein Y is derived from a monoisocyanate selected from the group consisting of hexyl isocyanate, 6-chlorohexyl isocyanate, n-octyl isocyanate, cyclohexyl isocyanate, 2-ethylhexyl isocyanate, 2,3,4-methylcyclohexyl isocyanate, 3,3,5-trimethylcyclohexyl isocyanate, 2-norbornyl-methyl isocyanate, decyl isocyanate, dodecyl isocyanate, tetradecyl isocyanate, hexadecyl isocyanate, octadecyl isocyanate, 3-butoxypropyl isocyanate, 3-(2-ethylhexyloxy)-propyl isocyanate, phenyl isocyanate, tolyl isocyanates, chlorophenyl isocyanates (2,3,4-isomers), dichlorophenyl isocyanates, 4-nitrophenyl isocyanate, 3-trifluoromethylphenyl isocyanate, benzyl isocyanate, dimethylphenyl isocyanates (commercial mixture and individual isomers), 4-dodecylphenyl isocyanate, 4-cyclohexyl-phenyl isocyanate, 1-naphthyl isocyanate, isocyanatoamides of 1 mol of diisocyanates and 1 mol of monocarboxylic acids, preferably of toluene diisocyanates, diphenylmethane diisocyanates and hexamethylene diisocyanate with aliphatic monocarboxylic acids, (6-isocyanatohexyl)-stearic acid amide, (3-isocyanatotolyl)-stearic acid amide, (6-isocyanatohexyl)-benzamide, and mixtures thereof; or
Y is derived from an aromatic, araliphatic, aliphatic or cycloaliphatic polyisocyanate having an NCO functionality of ≥2; or
Y is derived from a polyurethane prepolymer.

* * * * *